(12) United States Patent
Gouma

(10) Patent No.: US 8,980,640 B2
(45) Date of Patent: Mar. 17, 2015

(54) SELECTIVE CHEMOSENSORS BASED ON THE FERROELECTRIC MATERIALS, MIXED OXIDES, OR TEMPERATURE MODULATION OF OXIDE POLYMORPH STABILITY

(75) Inventor: Pelagia-Irene Gouma, Port Jefferson, NY (US)

(73) Assignee: The Research Foundation of State University of New York, Albany, NY (US)

( * ) Notice: Subject to any disclaimer, the term of this patent is extended or adjusted under 35 U.S.C. 154(b) by 219 days.

(21) Appl. No.: 13/511,858

(22) PCT Filed: Dec. 2, 2010

(86) PCT No.: PCT/US2010/058719
§ 371 (c)(1),
(2), (4) Date: Dec. 11, 2012

(87) PCT Pub. No.: WO2011/071746
PCT Pub. Date: Jun. 16, 2011

(65) Prior Publication Data
US 2013/0115706 A1    May 9, 2013

Related U.S. Application Data

(60) Provisional application No. 61/265,989, filed on Dec. 2, 2009.

(51) Int. Cl.
*G01N 33/00* (2006.01)
*G01N 33/20* (2006.01)
*G01N 27/12* (2006.01)
*G01N 33/497* (2006.01)

(52) U.S. Cl.
CPC .......... *G01N 27/125* (2013.01); *G01N 33/0031* (2013.01); *G01N 33/497* (2013.01); *G01N 2800/042* (2013.01)
USPC ............. 436/83; 436/103; 436/116; 436/130; 436/141; 436/142; 436/181; 422/83; 422/84; 422/88

(58) Field of Classification Search
CPC ... G01N 27/12; G01N 27/125; G01N 27/127; G01N 27/26; G01N 2800/00; G01N 2800/042; G01N 33/0027; G01N 33/0031; G01N 33/497
USPC ............... 436/63, 73, 83, 103, 130, 141, 142, 436/181, 116; 422/83, 84, 88, 98
See application file for complete search history.

(56) References Cited

U.S. PATENT DOCUMENTS 7,017,389 B2 *   3/2006   Gouma ........................ 73/31.05
2008/0077037 A1 *   3/2008   Gouma et al. ................ 600/532

OTHER PUBLICATIONS

Balazsi et al. Journal of the European Ceramic Society, vol. 28, 2008, pp. 913-917.*
Jimenez et al., "$NH_3$ Interaction with Catalytically Modified Nano-$WO_3$ Powders for Gas Sensing Applications," *Journal of Electrochemical Society*, vol. 150, No. 4 (2003), pp. H72-H80.
Kumar et al., "Structure, ferroelectric and gas sensing properties of Sol-gel derived $(Ba,Sr)(Ti,Zr)O_3$ thin films," *Materials Chemistry and Physics, Elsevier*, vol. 107, No. 2-3 (2007), pp. 399-403.
Shen et al., "Large-scale synthesis and gas sensing application of vertically aligned and double-sided tungsten oxide nanorod arrays," *Sensors and Actuators B: Chemical, Elsevier*, vol. 143, No. 1 (2009), pp. 325-332.
Wang et al., "Ferroelectric $WO_3$ Nanoparticles for Acetone Selective Detection," *Chemistry of Materials*, vol. 20, No. 15 (2008), pp. 4794-4796.

* cited by examiner

*Primary Examiner* — Maureen Wallenhorst
(74) *Attorney, Agent, or Firm* — Preti Flaherty Beliveau & Pachios LLP

(57) ABSTRACT

The present invention relates to gas sensors using doped ferroelectric materials. The sensors can be fabricated as an array where different portions of the array can operate at different independently controlled temperatures to detect different gas phase components of a gas sample. Preferred embodiments can be used for the diagnosis of conditions, such as, diabetes.

17 Claims, 1 Drawing Sheet

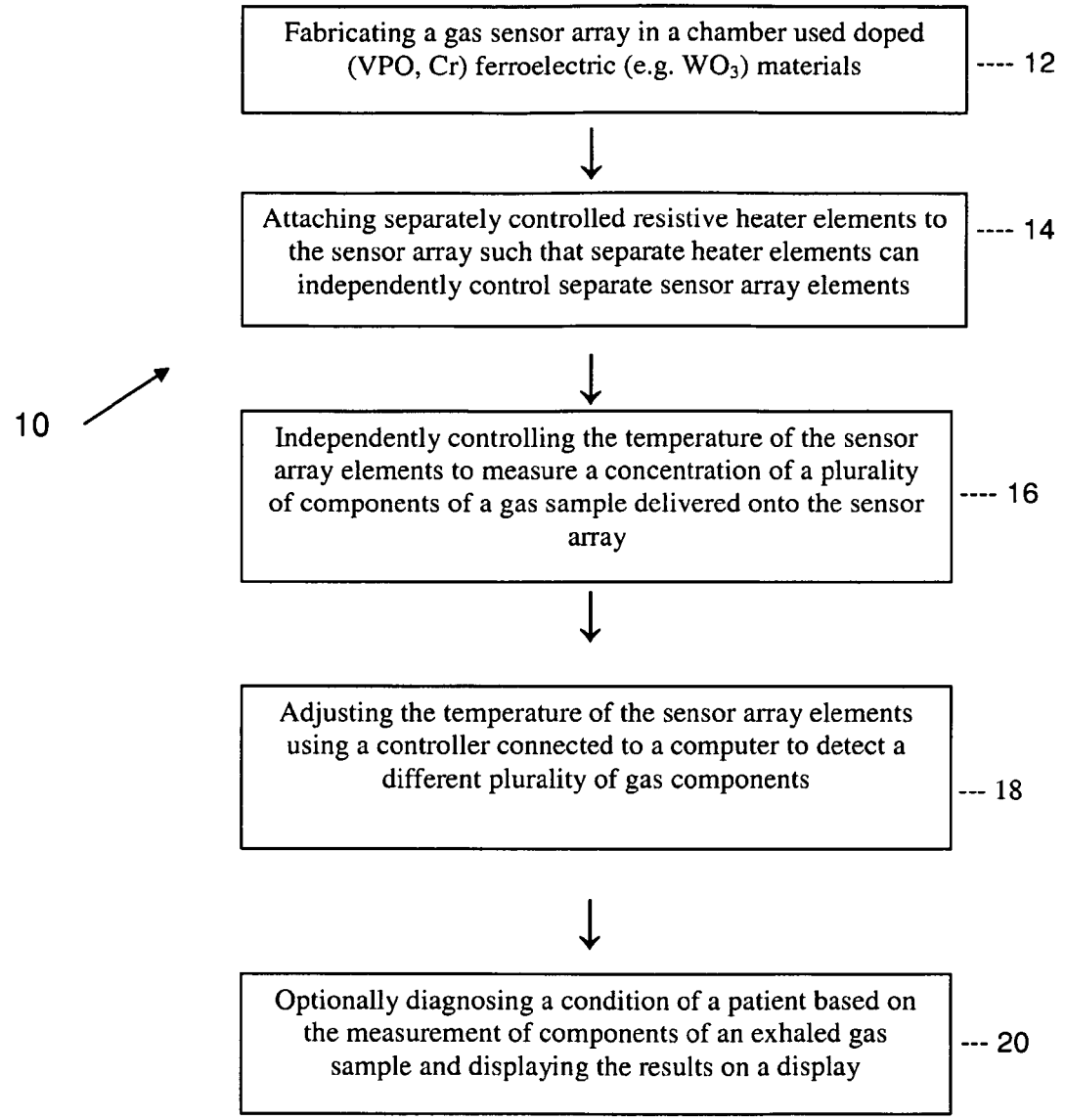

US 8,980,640 B2

SELECTIVE CHEMOSENSORS BASED ON THE FERROELECTRIC MATERIALS, MIXED OXIDES, OR TEMPERATURE MODULATION OF OXIDE POLYMORPH STABILITY

CROSS REFERENCE TO RELATED APPLICATION

This application claims priority to U.S. Provisional Application No. 61/265,989 filed on Dec. 2, 2009. The entire content of the above application is incorporated herein by reference.

STATEMENT REGARDING FEDERALLY SPONSORED RESEARCH OR DEVELOPMENT

This invention was made with government support under grant number DMR0304169 awarded by the National Science Foundation. The government has certain rights in the invention.

BACKGROUND OF THE INVENTION

Methods have been developed for the detection of gases using chemical sensors such as those described in "Ferroelectric $WO_3$ Nanoparticles for Acetone Selective Detection," by Wang et al., Chem. Mater., 20, 4794-4796 (2008), the entire contents of which is incorporated herein by reference. Further improvements in devices and methods of making and using such devices are needed, however, to improve the accuracy thereof, particularly for diagnostic applications.

SUMMARY OF THE INVENTION

The present invention relates to methods of fabrication and use of sensors to detect components of a gas sample. Doped ferroelectric materials such as $WO_3$ doped with VPO or Cr can be used to fabricate sensor arrays. The sensor array can be thermally coupled to a heater array such as a one or two dimensional (2D) matrix of resistive heater elements. The temperatures of the individual heater elements can be separately controlled to adjust the operating temperature of each heater element. Details regarding the fabrication of gas sensors can be found in "An Acetone Nanosensor for Non-invasive Diabetes Detection," by Wang et al. in the Proceedings of the 13$^{th}$ International Symposium by the American Institute for Physics, May 23, 2009, Vol. 113 (Issue 1), pages 206-208, the entire contents of which is incorporated herein by reference.

Preferred embodiments of the invention provide for the quantitative measurement of the concentration of different components of a gas sample such as the exhaled gas of a mammalian subject to diagnose a medical condition. A first plurality of sensor array elements can be set at a first temperature or range of temperatures and a second plurality if sensor array elements can be set at a second temperature or range of temperature by an electronic controller.

BRIEF DESCRIPTION OF THE DRAWINGS

FIG. 1 illustrates a process flow sequence for method of making and using a sensor in accordance with preferred embodiments of the invention.

DETAILED DESCRIPTION OF THE INVENTION

Ferroelectric and mixed oxide gas sensors for selective (discriminatory) detection of metabolites in human breath, sweat, saliva, sputum, urine, eye fluid, all bodily excretions. Using a crystallochemical approach selective gas oxide interactions for different classes of gases and oxide crystallographic arrangements have been achieved. Based on the selective oxidation catalysis of hydrocarbons, discrimination between biomarkers such as ethane and isoprene may be readily achieved. One example is the use of Vanadium Phosphorus Oxide (VPO) nanoparticles as catalytic dopants for the selective detection of ethane by rutile oxide structures. Using rapid solidification nanoscale synthesis routes, such as flame spray pyrolysis, efficient dispersion of vanadium active sites can be arranged across a sensing surface.

Selective acetone detection by ferroelectric $\epsilon$-$WO_3$ nanoparticles can be used in preferred embodiments of the invention. Recently, attention has been paid on the surface chemistry of ferroelectric materials. For example, research based on $LiNbO_3$ and other materials has shown that the dipole moment of a polar molecule can interact with the electric polarization of some ferroelectric domains on the surface. This interaction increases the strength of molecular adsorption on the material surface. Here, preferred embodiments employ the acentric structure of $\epsilon$-$WO_3$ which plays an important role on the selective detection of acetone. The $\epsilon$-$WO_3$ is a type of ferroelectric material having a spontaneous electric dipole moment. The polarity comes from the displacement of tungsten atoms from the center of each $[WO_6]$ octahedra. On the other hand, acetone has a much larger dipole moment than other gases. As a consequence, the interaction between the $\epsilon$-$WO_3$ surface dipole and acetone molecules is much stronger than other gases, leading to the observed selectivity to acetone detection.

Preferred embodiments use a single crystalline (polymorphic) binary oxide is sufficient to build multisensor arrays for the selective detection of several gaseous species at the same time, by simply individually controlling the temperature at which the stabilization heat treatment and the sensing process takes place through the use of resistive heaters incorporated to each sensor substrate. Hexagonal h-$WO_3$ material can be used for $NO_x$ (a nitrogen oxide compound) selective detection at 150° C. and for isoprene selective detection at 350° C. Individual sensor elements can be paired with heater elements to a form a 2D matrix array.

A method of fabricating and subsequently using 10. A sensor array is illustrated in connection with FIG. 1. The gas sensor array can be formed by doping a ferroelectric material 12 with a dopant at a concentration selected for a particular gas species. The sensor array can have a matrix of elements that can be independently readout to a computer for display. The sensor array can be attached 14 to an array of resistive heater elements where the temperature of each heater element can be independently controlled 16. By adjusting the temperature of separate sensor array elements to different first and second temperatures with an electronic controller connected to the heater array, for example, the concentration of different gas components can be measured 18 simultaneously or in temporal sequence. The results can be stored in memory and displayed 20 and be used for diagnosis of a patient.

The claims should not be read as limited to the described order or elements unless stated to that effect. Therefore, all embodiments that come within the scope and spirit of the following claims and equivalents thereto are claimed as the invention.

What is claimed is:
1. A method of detecting a gas with a gas sensor assembly, the method comprising:

delivering a gas sample onto a gas sensor, the sensor including a VPO doped $WO_3$ material for measuring a component of the gas sample.

2. The method of claim 1 wherein the sensor is one of an array of sensor elements, the method further comprising detecting a concentration of a gas component using the array of sensor elements.

3. The method of claim 2 wherein the gas sensor assembly further comprises a heater array attached to the array of sensor elements, the method further comprising using the heater array for controlling a temperature of the sensor elements.

4. The method of claim 3 further comprising adjusting the temperature of a first sensor element of the array of sensor elements to a first temperature for detecting a first gas component and simultaneously adjusting the temperature of a second sensor element of the array of sensor elements to a second temperature that is different from the first temperature for detecting a second gas component.

5. The method of claim 4 further comprising detecting a first sample with the temperature of at least one sensor element of the array of sensor elements at 150° C.

6. The method of claim 4 further comprising detecting a second sample with the temperature of at least one sensor element of the array of sensor elements at 350° C.

7. The method of claim 3 wherein the heater array further comprises a matrix array of heater elements thermally coupled to the array of sensor elements, the step of using the heater array comprises individually controlling the temperature of the matrix array of heater elements.

8. The method of claim 3 further comprising adjusting the temperature of the array of sensor elements with an electronic controller.

9. The method of claim 2 further comprising detecting a concentration of a nitrogen oxide compound ($NO_x$) using at least one sensor of the array of sensor elements.

10. The method of claim 2 further comprising detecting a concentration of isoprene using at least one sensor of the array of sensor elements.

11. The method of claim 2 further comprising detecting a concentration of ethane using at least one sensor of the array of sensor elements.

12. The method of claim 2 further comprising detecting a concentration of acetone using at least one sensor of the array of sensor elements.

13. The method of claim 1 further comprising detecting an exhaled gas sample from a mammalian subject using the sensor to detect a medical condition.

14. The method of claim 1 further comprising detecting a quantitative concentration of a gas component and recording data in a memory of a computer.

15. The method of claim 1 wherein the sensor comprises nanoparticles of a tungsten oxide compound.

16. The method of claim 1 wherein the sensor comprises $\epsilon\text{-}WO_3$.

17. The method of claim 1 wherein the sensor comprises $h\text{-}WO_3$.

* * * * *